US008034971B2

(12) United States Patent  (10) Patent No.: US 8,034,971 B2
Niitani                    (45) Date of Patent:    Oct. 11, 2011

(54) METHOD FOR PRODUCING 1,2-PHENYLETHANE COMPOUND USING ATOM TRANSFER RADICAL COUPLING REACTION

(75) Inventor: Takeshi Niitani, Ichihara (JP)

(73) Assignee: Nippon Soda Co., Ltd., Tokyo (JP)

(*) Notice: Subject to any disclaimer, the term of this patent is extended or adjusted under 35 U.S.C. 154(b) by 268 days.

(21) Appl. No.: 12/225,217

(22) PCT Filed: Mar. 16, 2007

(86) PCT No.: PCT/JP2007/055393
§ 371 (c)(1),
(2), (4) Date: Sep. 15, 2008

(87) PCT Pub. No.: WO2007/119402
PCT Pub. Date: Oct. 25, 2007

(65) Prior Publication Data
US 2009/0275772 A1    Nov. 5, 2009

(30) Foreign Application Priority Data
Mar. 17, 2006 (JP) ................. 2006-074463

(51) Int. Cl.
*C07C 69/76* (2006.01)
(52) U.S. Cl. ..................................... 560/101
(58) Field of Classification Search .......... None
See application file for complete search history.

(56) References Cited

U.S. PATENT DOCUMENTS
6,566,548 B1   5/2003   Abe et al.

FOREIGN PATENT DOCUMENTS
EP    1 120 391       8/2001
JP    57-065716       4/1982
JP    07-076538       3/1995
WO    WO 2000/023072  4/2000

OTHER PUBLICATIONS

Johnson, David K.; Ciavarri, Jeffrey P.; Ishmael, Faoud T.; Schillinger, Kurt J.; van Geel, Thomas A. P.; Stratton, Stephen M., A novel copper(I) mediated, symmetrical coupling procedure for alkyl, aryl, benzyl, and thiophenyl dihalides, Tetrahedron Letters (1995), 36(47), 8565-8.*
Silverman, R., The Organic Chemistry of Drug Design and Drug Action, 1992, Academic Press Inc.*
Sayles, D. C.; Kharasch, M. S., The synthesis of symmetrically substituted ethane derivatives, Journal of Organic Chemistry (1961), 26, 4210-14.*
Casreact abstract, Accession No. 56:53067, Sayles, D. C.; Kharasch, M. S., The synthesis of symmetrically substituted ethane derivatives, Journal of Organic Chemistry (1961), 26, 4210-14.*
Pri-Bar, IIa, Transformation of carbinols by dichlorotris(triphenylphosphine)ruthenium and by some other transition-metal catalysts, Journal of Organic Chemistry (1980), 45(22), 4418-28.*
Inductive Effect Printout http://en.wikipedia.org/wiki/Inductive_effect.*

Japanese Patent Office, International Search Report (translated) dated May 1, 2007, from related International Patent Application No. PCT/JP2007/055393 , filed on Mar. 16, 2007 (in Japanese).
Japanese Patent Office, International Preliminary Report on Patentability and Written Opinion (translated) dated Oct. 21, 2008, from related International Patent Application No. PCT/JP2007/055393 , filed on Mar. 16, 2007 (in Japanese).
Chwala and Bartek, "Über einige Kondensationsreaktionen des Glyoxals, " Monatshefte fur Chem I e., 82, 652-655 (1951).
T. Osako et al., "Carbon-Halogen Bond Activation Mechanism by Copper(I) Complexes of (2-Pyridyl)alkylamine Ligands," *Inorg. Chem.*, 2005, vol. 44, pp. 410-415.
Jean-March Kern et al., "Photoassisted C-C Coupling via Electron Transfer to Benzylic Halides by a Bis(di-imine) Copper(i) Complex," *J. Chem. Soc., Chem. Comm.*, 1987, pp. 546-548.
Khurana et al., "Facile reductive coupling of benzylic halides with ferrous oxalate dihydrate," *Organic and Biomolecular Chemistry*, vol. 1, pp. 1737-1740, 2003.
Li et al., "Ruthenium-catalyzed carbon-carbon formation to synthesize tetraarylethanes and tetraarylxylylene through dechlorinative dimeric reaction," *Journal of Organometallic Chemistry*, 687, pp. 12-15, 2003.

(Continued)

*Primary Examiner* — Daniel Sullivan
*Assistant Examiner* — Jennifer C Sawyer
(74) *Attorney, Agent, or Firm* — Kenyon & Kenyon LLP

(57) ABSTRACT

An object of the present invention is to provide a method capable of producing a 1,2-phenylethane compound with extremely high yield in a short amount of time. Disclosed is a method for producing a 1,2-phenylethane compound, which comprises subjecting a compound represented by formula (I):

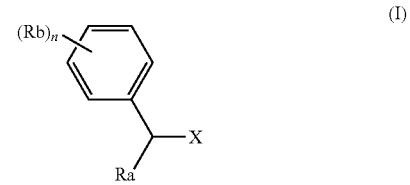

wherein Ra represents a hydrogen atom or a substituted or unsubstituted phenyl group; Rb represents a hydrogen atom or a substituent; n represents an integer of 1 to 5 and, when n is 2 or more, Rb may be the same or different, or may be combined with each other to form a ring; and X represents a halogen atom; to a coupling reaction in the presence of a transition metal complex to produce a compound represented by formula (II):

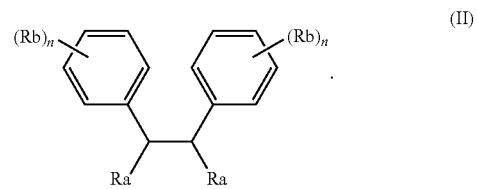

6 Claims, No Drawings

OTHER PUBLICATIONS

Francalanci et al., "Phase-transfer catalysis in cobalt catalyzed carbonylation of secondary benzyl halides," *Journal of Electroanalytical Chemistry*, vol. 232, pp. 59-70, 1982.

Whitmore et al., "The reaction of organic mercury compounds with organic halides. II[1]," *Journal of the American Chemical Society*, vol. 51, No. 5, pp. 1491-1503, May 1, 1929.

Li et al., "Ruthenium-catalyzed coupling reaction of benzylic halides," *Synthetic Communications*, vol. 33, No. 20, pp. 3583-3588, Oct. 20, 2003.

Liu et al., "Tuning the electrical conductivity and self-assembly of regioregular polythiophene by block copolymerization: Nanowire morphologies in new di- and triblock copolymers," *Angewandte Chemie International English Edition*, vol. 41, No. 2, 2002.

To et al., "Solvent dependence of the evolution of the surface morphology of thin asymmetric diblock copolymer films," *Thin Solid Films*, vol. 467, pp. 59-64, 2004.

Search Report, European Application No. EP 07 73 8838 dated Aug. 26, 2010.

* cited by examiner

METHOD FOR PRODUCING 1,2-PHENYLETHANE COMPOUND USING ATOM TRANSFER RADICAL COUPLING REACTION

TECHNICAL FIELD

This application is a national stage filing (35 U.S.C. §371) OF PCT/JP2007/055393, filed on Mar. 16, 2007, which claims priority on Japanese Patent Application No. 2006-074463 filed on Mar. 17, 2006, the disclosure of which is incorporated by reference herein.

The present invention relates to a method for producing a 1,2-phenylethane compound, and particularly to a method for producing a 1,2-phenylethane compound using a transition metal compound as a catalyst.

BACKGROUND ART

Tetrakis (hydroxyphenyl)alkane can be used as a host compound in polymolecular clathrate compounds. For example, 1,1,2,2-tetrakis (4-hydroxyphenyl)ethane selectively forms clathrate compounds (compounds having an inclusion of guest molecule in a cavity formed by the host molecule) with various organic guest compounds and therefore it's application is expected in technical fields such as selective separation, chemical stabilization, prevention of vaporization and pulverization.

Up until the present, as a method for producing tetrakis (hydroxyphenyl)alkanes, a method of condensing phenol and glyoxal in acetic acid in a temperature range of 2 to 10° C. in the presence of sulfuric acid is known (for example, Non-Patent Document 1).

In addition, there is a method for producing tetrakis(hydroxyphenyl)alkanes by condensing glyoxal and phenol in excess with respect to glyoxal in a temperature range of 100 to 180° C. in the presence of hydrochloric acid (for example, Patent Document 1) or a method characterized by condensing phenol and a dialdehyde or derivatives thereof in the presence of sulfuric acid and phosphoric acid (for example, Patent Document 2).

However as shown by the method disclosed in Patent Document 1, a reaction using a single sulfuric acid catalyst is difficult to control and tends to be associated with side reactions or runaway reactions. Furthermore although reactions at high temperatures using phenol in excess have characters such as no requirement of reaction solvents, a short reaction time and a low cost, there is a tendency for side reactions and high yields are not expected. Moreover there is the problem that it is extremely difficult to eliminate multiple products resulting from such side reactions.

As shown by the method disclosed in Patent Document 2, side reactions can be suppressed by condensation in the presence of a mixed acidic catalyst comprising sulfuric acid and phosphoric acid resulting in highly efficient and selective production of tetrakis(hydroxyphenyl)alkanes. However, the yield is on the order of 40 to 70% and the reaction time requires from several to tens of hours.

As shown by the method disclosed in Patent Document 3, a compound having a tetrakis phenyl backbone combining ester groups with phenyl groups can be produced by a coupling reaction using a zinc catalyst. However this method requires a 24-hour reflux process, and has a long reaction time and a low yield.

Non-Patent Document 1:
Monatshefte fur Chem I e., 82, 652 (1951)
Patent Document 1:
Japanese Unexamined Patent Application, First Publication No. Sho-57-65716
Patent Document 2:
Japanese Unexamined Patent Application, First Publication No. Hei-7-076538
Patent Document 3:
WO 00/20372

DISCLOSURE OF THE INVENTION

An object of the present invention is to provide a method for producing a 1,2-phenylethane compound in a short reaction time and with an extremely high yield.

The present inventors conducted diligent research into solving the above problems and completed the present invention based on the insight that it is possible to produce a 1,2-phenylethane compound using an atom transfer radical coupling reaction using a transition metal complex catalyst. As a result, it is possible to produce a 1,2-phenylethane compound in a extremely shorter reaction time and higher yield in comparison to a coupling method using zinc or another conventional method.

Namely, the present invention relates to the following:

[1] A method for producing a 1,2-phenylethane compound, which comprises subjecting a compound represented by formula (I):

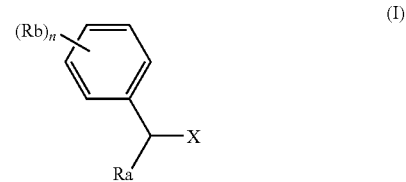

wherein Ra represents a hydrogen atom or a substituted or unsubstituted phenyl group; Rb represents a hydrogen atom or a substituent; n represents an integer of 1 to 5 and, when n is 2 or more, Rb may be the same or different, or may be combined with each other to form a ring; and X represents a halogen atom; to a coupling reaction in the presence of a transition metal complex to produce a compound represented by formula (II):

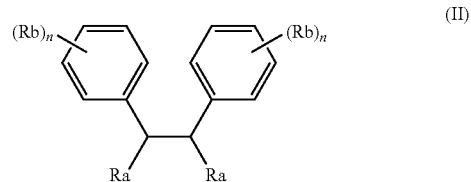

[2] The method for producing a 1,2-phenylethane compound according to the above-described [1], wherein Ra is a substituted or unsubstituted phenyl group; and

[3] The method for producing a 1,2-phenylethane compound according to the above-described [1] or [2], wherein the substituent of the phenyl group represented by Ra or the substituent represented by Rb is $COOR^1$, $SO_2R^2$, $OR^3$, $SR^4$ or $N(R^5)(R^6)$, ($R^1$ to $R^6$ represent a hydrogen atom or an organic group).

Furthermore, the present invention relates to the following:

[4] The method for producing a 1,2-phenylethane compound according to any one of the above-described [1] to [3], wherein the compound represented by formula (I) is a compound represented by formula (I-1):

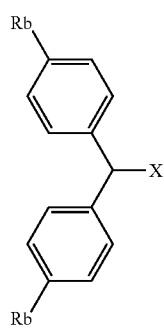

(I-1)

and the compound represented by formula (II) is a compound represented by formula (II-1):

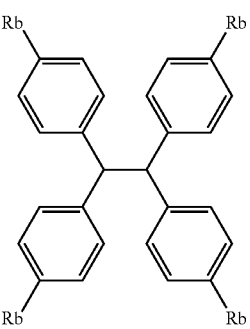

(II-1)

[5] The method for producing a 1,2-phenylethane compound according to the above-described [4], wherein Rb in formula (I-1) or (II-1) is $OR^3$ or COORS; and

[6] The method for producing a 1,2-phenylethane compound according to any one of the above-described [1] to [5], wherein the transition metal complex is a copper complex or an iron complex.

The method according to the present invention allows production of a 1,2-phenylethane compound in an extremely short amount of time with a high yield.

BEST MODE FOR CARRYING OUT THE INVENTION

A method for producing a 1,2-phenylethane compound according to the present invention is not particularly limited as long as it is a method in which a compound represented by formula (I):

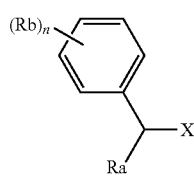

(I)

is subjected to a coupling reaction in the presence of a transition metal complex to produce a compound represented by formula (II):

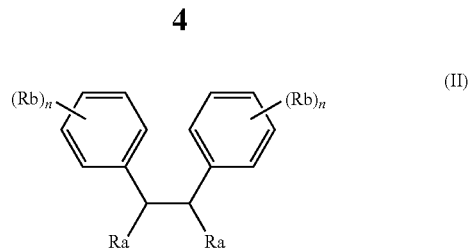

(II)

According to the present invention, it is possible to obtain the compound represented by formula (II) in an extremely short amount of time with a high yield. One compound or more than one compound can be used as the compound represented by formula (I). The coupling reaction of the present invention can be homo-coupling or cross-coupling.

Ra in formula (I) or (II) represents a hydrogen atom or a substituted or unsubstituted phenyl group. From the point of reactivity, a substituted or unsubstituted phenyl group is preferred. When there are two or more substituents in phenyl groups, the substituents may be the same or different, or may be connected each other and form saturated rings, aromatic rings or heterocycles. Rb represents a hydrogen atom or a substituent. n represents an integer of 1 to 5 and, when n is 2 or more, Rb may be the same or different, or may be combined with each other to form a saturated ring, an aromatic ring or a heterocycle. X represents a halogen atom and includes, for example, chlorine atoms, bromine atoms and iodine atoms. From the point of reactivity, bromine atoms are preferred.

The substituent of the phenyl group represented by Ra or the substituent represented by Rb includes, for example, $COOR^1$, $SO_2R^2$, $OR^3$, $SR^4$ or $N(R^5)(R^6)$. $COOR^1$ is preferred. $R^1$ to $R^6$ represent a hydrogen atom or an organic group. The organic group includes, for example, an alkyl group, a silyl group, an acyl group, an aryl group, a phosphoryl group, a sulfonyl group, an alkylphosphoryl group or an alkylsulfonyl group. Concretely, the substituent includes alkoxy groups such as a methoxy group or an ethoxy group, a silyloxy group such as a trimethylsilyloxy group, t-butyl-dimethylsilyloxy group or a dimethylphenylsilyloxy group, an acyl group such as an acetyl group or a benzoyl group, or an aryloxy group such as a phenoxy group or a naphthoxy group.

In particular, $R^3$ can be a methyl group, a methoxymethyl group, a 2-methoxyethoxymethyl group, a methylthiomethyl group, a tetrahydropyranyl group, a phenacyl group, a cyclopropylmethyl group, an allyl group, an isopropyl group, a cyclohexyl group, a t-butyl group, a benzyl group, an ortho-nitrobenzyl group, a 9-anthrylmethyl group, a 4-picolyl group, a trimethylsilyl group, a t-butyl-dimethylsilyl group, an acetyl group, a benzoyl group, a valeryl group, a 2,2,2-trichloroethylcarbonyl group, a vinylcarbonyl group, a benzylcarbonyl group, an aryl carbamoyl group, a methanesulfonyl group, and a toluenesulfonyl group.

A preferred form of the compound is shown in formula [1].

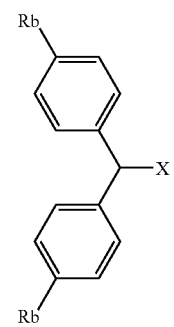

(I-1)

The compound shown in formula [1] includes the compound shown in formula [I-1].

A coupling reaction with the compound shown in formula [I-1] gives:

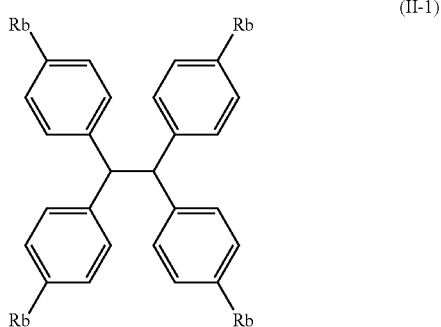

(II-1)

The compound shown in formula (II-1) can be obtained by above-mentioned coupling reaction.

The transition metal complex of the present invention includes, for example, a catalyst which can be used in a living radical polymerization method. In the method according to the present invention, the transition metal complex may be added directly to the system or a metal compound and a ligand compound thereof can be added to the system in order to form a transition metal complex in the system.

The central metals forming the transition metal complex include elements from Groups 7 to 11 of the Periodic Table such as manganese, rhenium, iron, ruthenium, rhodium, nickel or copper (using the periodic table disclosed in "Handbook of Chemistry I, Basic, 4th revised edition" (1993), edited by The Chemical Society of Japan). Use of copper and iron is preferred from among these metals with the use of copper being particularly preferred.

Concretely, the copper complex includes copper complexes having nitrogen-containing compounds as ligands, such as $NH_3$, NO, $NO_2$, $NO_3$, ethylenediamine, diethylenetriamine, tributylamine, 1,3-diisopropyl-4,5-dimethylimidazol-2-ylidene, pyridine, phenanthroline, diphenanthroline or substituted phenanthroline, 2,2':6',2"-terpyridine, pyridine imine, cross-linked aliphatic diamine, 4-4'-di(5-nonyl)-2,2'-bipyridine, thiocyanate, bipyridine coordinated with O, S, Se or Te, iminodipyridine, alkyliminopyridine, alkylbipyridinylamine, alkyl-substituted tripyridine, di(alkylamino)alkyl pyridine, ethylenediamine dipyridine, tri(pyridinylmethyl) amine, N,N,N',N',N"-pentamethyl diethylene triamine. Furthermore, the copper complexes include copper complexes having above nitrogen-containing compounds and/or halogen atom as ligands. Concretely, it includes acetyl-[4-4'-di(5-nonyl)-2,2'-bipyridine]copper, hexafluorophosphine-di[4-4'-di(5-nonyl)-2,2'-bipyridine]copper, thiocyanate copper and N,N,N',N',N"-pentamethyl diethylene triamine copper bromide.

The iron complex includes di(triphenylphosphine) iron dichloride, di(tributylamino) iron dichloride, triphenylphosphine iron trichloride, (1-bromo)ethylbenzene-triethoxyphosphine-iron dibromide, (1-bromo)ethylbenzene-triphenylphosphine-iron dibromide, (1-bromo)ethylbenzene-[4-4'-di(5-nonyl)-2,2'-bipyridine] iron dibromide, (1-bromo) ethylbenzene-tri-n-butylamino-iron dibromide, (1-bromo) ethylbenzene-tri-n-butylphosphine-iron dibromide, tri-n-butylphosphine-iron dibromide, [4-4'-di(5-nonyl)-2,2'-bipyridine] iron dibromide, tetraalkylammonium iron(II) trihalide, dicarbonylcyclopentadienyl iron(II) iodide, dicarbonylcyclopentadienyl iron(II) bromide, dicarbonylcyclopentadienyl iron(II) chloride, dicarbonylindenyl iron(II) iodide, dicarbonylindenyl iron(II) bromide, dicarbonylindenyl iron(II) chloride, dicarbonylfluorenyl iron(II) iodide, dicarbonylfluorenyl iron(II) bromide, dicarbonylfluorenyl iron(II) chloride, 1,3-diisopropyl-4,5-dimethylimidazol-2-ylidene iron chloride and 1,3-diisopropyl-4,5-dimethylimidazol-2-ylidene iron bromide.

Other transition metal complexes include ruthenium complexes such as dichlorotris(triphenylphosphine) ruthenium, dichlorotris(tributylphosphine) ruthenium, dichloro(trialkylphosphine) p-cymene ruthenium, dichloro-di(tricymenephosphine)styryl ruthenium, dichloro(cyclooctadiene) ruthenium, dichlorobenzene ruthenium, dichloro p-cymene ruthenium, dichloro(norbornadiene) ruthenium, cis-dichloro-bis(2,2'-bipyridine) ruthenium, dichlorotris(1,10-phenanthroline) ruthenium, carbonylchlorohydridetris(triphenylphosphine) ruthenium, chlorocyclopentadienylbis (triphenylphosphine) ruthenium, chloroindenylbis (triphenylphosphine) ruthenium, dihydrotetra (triphenylphosphine) ruthenium, dicarbonylcyclopentadienyl ruthenium(II) iodine, dicarbonylcyclopentadienyl ruthenium(II) bromide, dicarbonylcyclopentadienyl ruthenium(II) chloride, dicarbonylindenyl ruthenium(II) iodine, dicarbonylindenyl ruthenium(II) bromide, dicarbonylindenyl ruthenium(II) chloride, dicarbonylfluorenyl ruthenium(II) iodine, dicarbonylfluorenyl ruthenium (II) bromide, dicarbonylfluorenyl ruthenium (II) chloride and dichloro-di-2,6-bis[(dimethylamino)-methyl] ($\mu$-$N_2$) pyridine ruthenium(II).

Nickel complexes include carbonylcyclopentadienyl nickel (II) iodine, carbonylcyclopentadienyl nickel (II) bromide, carbonylcyclopentadienyl nickel (II) chloride, carbonylindenyl nickel (II) iodine, carbonylindenyl nickel(II) bromide, carbonylindenyl nickel(II) chloride, carbonylfluorenyl nickel (II) iodide, carbonylfluorenyl nickel(II) bromide, carbonylfluorenyl nickel(II) chloride, o,o'-di(dimethylaminomethyl)phenyl nickel halide, di-triphenylphosphine nickel dibromide, di(tri-n-butylamino) nickel dibromide, 1,3-diaminophenyl nickel bromide, di(tri-n-butylphosphine) nickel dibromide and tetra (triphenylphosphine) nickel.

Further complexes include molybdenum complexes including tricarbonylcyclopentadienyl molybdenum(II) iodine, tricarbonylcyclopentadienyl molybdenum (II) bromide, tricarbonylcyclopentadienyl molybdenum (II) chloride, di-N-aryl-di(2-dimethylaminomethylphenyl) lithium molybdenum, di-N-aryl-(2-dimethylaminomethylphenyl)-methyl-lithium molybdenum, di-N-aryl-(2-dimethylaminomethylphenyl)-trimethylsilylmethyl-lithium molybdenum, di-N-aryl-(2-dimethylaminomethylphenyl)-p-tolyl lithium molybdenum; tungsten complexes including tricarbonylcyclopentadienyl tungsten(II) iodine, tricarbonylcyclopentadienyl tungsten (II) bromide, tricarbonylcyclopentadienyl tungsten (II) chloride; cobalt complexes including dicarbonylcyclopentadienyl cobalt(I); manganese complexes including tricarbonylcyclopentadienyl manganese(I), tricarbonyl(methylcyclopentadienyl) manganese(I); rhenium complexes including tricarbonylcyclopentadienyl rhenium (I), dioxobis (triphenylphosphine) rhenium iodine; rhodium complexes including tri(triphenylphosphine) rhodium chloride; palladium complexes including triphenylphosphine diacetyl palladium. These transition metal complexes may be used singly or in combination.

The amount of transition metal compound added depends on the type of compound. However it is generally preferable to add 0.1 to 5 equivalents to the compound acting as a raw material represented by formula (I) and more preferably to add 0.3 to 1 equivalents.

In the method according to the present invention, from the point of improving catalyst activity, it is preferable to perform the coupling reaction in the presence of a base. The base may be organic or inorganic. Organic bases include amines such as aliphatic amines or aromatic amines. Inorganic bases include alkali metal hydroxides or carbonates and alkaline earth metal oxides or carbonates.

There is no particular limitation on the organic solvent used in the reaction and it includes aromatic hydrocarbons such as benzene, toluene and xylene; aliphatic hydrocarbons such as hexane, heptane and octane; alicyclic hydrocarbons such as cyclopentane, cyclohexane and cyclooctane; ketones such as acetone, methyl ethyl ketone and cyclohexanone; ethers such as tetrahydrofuran and dioxane; esters such as ethyl acetate and butyl acetate; amides such as N,N-dimethylformamide and N,N-dimethylacetamide; sulfoxides such as dimethylsulfoxide; alcohol such as methanol and ethanol; polyvalent alcohol derivates such as ethylene glycol monomethyl ether and ethylene glycol monomethyl ether acetate. These solvents may be used singly or in combination.

The reaction temperature is normally from room temperature to 150° C. and preferably from 60 to 120° C. The reaction is normally performed under ordinary pressure or under pressurized conditions. Furthermore the reaction should proceed in an extremely short time and should reach completion in 3 to 90 minutes and preferably approximately 5 to 30 minutes. In this manner, the method of production of the present invention can produce the target compound in an extremely efficient manner. The reaction can be terminated by lowering the reaction temperature. After terminating the reaction, the target compound can be isolated by normal isolation and purification methods such as recrystallization, column purification, depressurization purification and filtration.

In the method of the present invention, when a produced compound represented by formula (II) has substituents such as $COOR^1$, $SO_2$, $OR^2$, $OR^3SR^4$ or $N(R^5)(R^6)$ on the benzene ring, active hydrogen is produced by acid treatment and it is possible to convert the substituents into COOH, $SO_2H$, OH, SH or $NH_2$. Furthermore, after hydrolysis in the presence of a base, it is possible to convert the substituents into OH or SH. Acids used in an acid treatment include inorganic acids such as hydrochloric acid, bromic acid, sulfuric acid, nitric acid, boric acid, methanesulfonic acid or organic acids such as acetic acid. The temperature during acid treatment is not particularly limited and may, for example, be in the range of −10° C. to 150° C. The base may be organic or inorganic. Organic, bases include, for example, amines such as aliphatic amines and aromatic amines. Inorganic bases include alkali metal hydroxides or carbonates and alkaline earth metal oxides and carbonates.

The present invention will be described in further detail hereafter. However the scope of the invention is not limited to the examples.

Example 1

PhCOOEt₂-Br

-continued

TEP-4COOEt 0.39 g (1 mmol) of PhCOOEt₂-Br, 0.14 g (1 mmol) of CuBr, 0.25 g (4 mmol) of Cu(0) and 20 mL of toluene were charged into a 50 mL reaction flask. After degassing the solution, 0.35 g (2 mmol) of N,N,N',N',N''-pentamethyldiethylenetriamine was added. The mixture was stirred at 80° C. for 0.5 h and cooled to room temperature. The insoluble matter was filtered and the reaction mixture was washed with water until the coloring was removed completely from the water layer, and dried over magnesium sulfate. The solvent was removed under reduced pressure to give 0.30 g of a white powder solid, finally, recrystallized (isolated yield 97%).

Example 2

1.15 g (5 mmol) of methyl 4-(bromomethyl)benzoate, 0.72 g (5 mmol) of CuBr, 1.27 g (20 mmol) of Cu(0), 1.56 g (10 mmol) of bipyridine and 20 ml of toluene were charged into a 30 mL reaction flask. After degassing the solution, the mixture was stirred at 100° C. for 1 h and cooled to room temperature. 10 mL of chloroform was added, and the insoluble matter was filtered and the reaction mixture was washed with water and dried over magnesium sulfate. The solvent was removed under reduced pressure and the crude product was recrystallized from ethyl acetate/hexane. The crystal thereby obtained was dried under reduced pressure to obtain 0.32 g of a faintly yellow crystal (isolated yield 43%).

Example 3

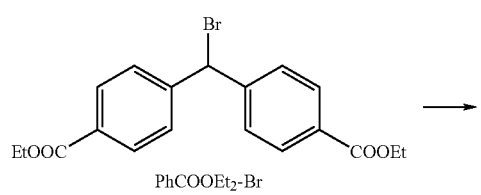

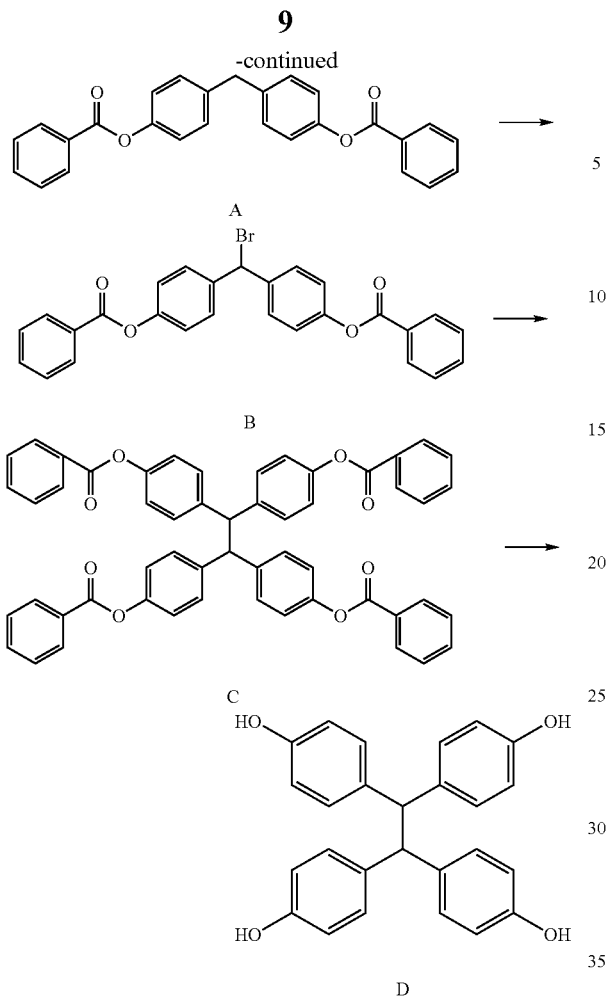

9.6 g (48 mmol) of bis(4-hydroxyphenyl)methane, 11.8 g (117 mmol) of triethylamine, 200 mL of tetrahydrofuran were charged into a 200 mL reaction flask and cooled to 0° C. 14.9 g (106 mmol) of benzoyl chloride was added and the mixture was stirred at room temperature for 1 hour. Triethylamine hydrochloride was removed by filtration and the reaction mixture was evaporated. After the residue was dissolved in methylene chloride, the reaction mixture was washed with water for three times, and dried over magnesium sulfate. After removal of solvent under reduced pressure, the crude product was recrystallized from hexane/ethyl acetate to give 16.8 g of a faintly yellow needle crystal A (isolated yield 86%).

14.4 g (35 mmol) of the crystal A, 6.5 g (37 mmol) of N-bromosuccinimide, and 70 mL of benzene were charged into a 200 mL reaction flask and refluxed for 1 hour. After cooling, the reaction mixture was concentrated under reduced pressure. The residue was dissolved in methylene chloride, washed with water for three times, and dried over magnesium sulfate. After removal of solvent under reduced pressure, the crude product was recrystallized from ethyl acetate to give 11.7 g of a white floccular crystal B (isolated yield 68%).

4.9 g (10 mmol) of the crystal B, 0.7 g (5 mmol) of CuBr, 1.3 g (20 mmol) of Cu, and 50 mL of toluene were charged into a 100 mL reaction flask. After degassing the solution and heating the solution to 80° C., 1.8 g (10 mmol) of N,N,N',N',N"-pentamethyl diethylene triamine was added. The mixture was stirred at 80° C. for 0.5 h and cooled to room temperature. The reaction mixture was filtered and the insoluble matter was washed with water for three times. 100 mL of chloroform was added to the insoluble matter, and refluxed for 10 minutes and filtered while still hot.

After the concentration of the filtrate, the crude product was washed with ethyl acetate to give 3.1 g of a white floccular crystal C (isolated yield 76%).

Then 2.6 g (3.2 mmol) of the crystal C, and 50 mL of toluene were charged into 100 mL reaction flask. Hydrolysis products saponified in the presence of potassium hydroxide and water were purified to give 1.1 g (2.8 mmol) of a white powder of 1,1,2,2-tetrakis(4-hydroxyphenyl)ethane D.

The invention claimed is:

1. A method for producing a 1,2-phenylethane compound, which comprises subjecting a compound represented by formula (I):

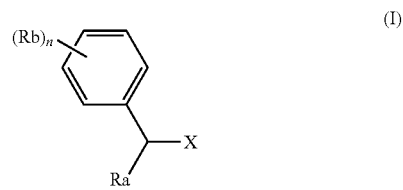

wherein Ra represents a hydrogen atom or a substituted or unsubstituted phenyl group; Rb represents a hydrogen atom or a substituent; n represents an integer of 1 to 5 and, when n is 2 or more, Rb may be the same or different, or may be combined with each other to form a ring; and X represents a halogen atom; to a coupling reaction in the presence of a transition metal complex to produce a compound represented by formula (II):

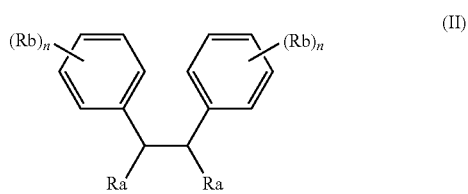

wherein the substituent of the phenyl group represented by Ra or the substituent represented by Rb is $COOR^1$, $SO_2R^2$, $OR^3$, $SR^4$ or $N(R^5)(R^6)$, and $R^1$ to $R^6$ represent a hydrogen atom or an organic group.

2. The method for producing a 1,2-phenylethane compound according to claim 1, wherein Ra is a substituted or unsubstituted phenyl group.

3. The method for producing a 1,2-phenylethane compound according to claim 1 or 2, wherein the compound represented by formula (I) is a compound represented by formula (I-1):

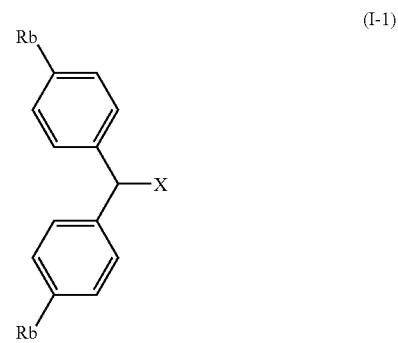

and the compound represented by formula (II) is a compound represented by formula (II-1):

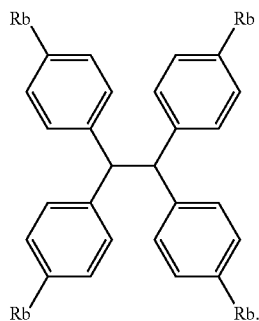

(II-1)

4. The method for producing a 1,2-phenylethane compound according to claim 3, wherein Rb in formula (I-1) or (II-1) is $OR^3$ or $COOR^1$, and $R^1$ and $R^3$ represent a hydrogen atom or an organic group.

5. The method for producing a 1,2-phenylethane compound according to claim 1 or 2, wherein the transition metal complex is a copper complex or an iron complex.

6. The method for producing a 1,2-phenylethane compound according to claim 1 or 2, wherein Cu(0) is further utilized.

* * * * *

UNITED STATES PATENT AND TRADEMARK OFFICE
CERTIFICATE OF CORRECTION

PATENT NO. : 8,034,971 B2
APPLICATION NO. : 12/225217
DATED : October 11, 2011
INVENTOR(S) : Takeshi Niitani It is certified that error appears in the above-identified patent and that said Letters Patent is hereby corrected as shown below:

In the Specifications:

In column 3, line 37 change "COORS" to --COOR$^1$--

In column 7, line 38 change "SO$_2$, OR$^2$, OR$^3$SR$^4$" to --SO$_2$R$^2$, OR$^3$, SR$^4$--

Signed and Sealed this
Fourth Day of June, 2013

Teresa Stanek Rea
*Acting Director of the United States Patent and Trademark Office*